United States Patent [19]

Bymaster et al.

[11] Patent Number: 5,858,393
[45] Date of Patent: Jan. 12, 1999

[54] TRANSDERMAL FORMULATION

[75] Inventors: Franklin Porter Bymaster, Brownsburg; Harlan E. Shannon, Carmel; Lisa A. Shipley, Fishers, all of Ind.; Kirti H. Valia, Plainsburo, N.J.

[73] Assignee: Eli Lilly and Company, Indianapolis, Ind.

[21] Appl. No.: 918,141

[22] Filed: Aug. 25, 1997

Related U.S. Application Data

[63] Continuation of Ser. No. 481,016, Jun. 7, 1995, abandoned, which is a continuation-in-part of Ser. No. 390,445, Feb. 17, 1995, abandoned.

[51] Int. Cl.$^6$ ...................................................... A61F 13/02
[52] U.S. Cl. ............................................ 424/448; 424/449
[58] Field of Search ..................................... 424/448, 449

[56] References Cited

U.S. PATENT DOCUMENTS

| | | | |
|---|---|---|---|
| 4,316,893 | 2/1982 | Rajadhyaksha | 424/180 |
| 5,130,319 | 7/1992 | Pinza et al. | 514/300 |
| 5,238,933 | 8/1993 | Catz et al. | 514/236.2 |
| 5,260,314 | 11/1993 | Sauerberg | 514/305 |

FOREIGN PATENT DOCUMENTS

| | | |
|---|---|---|
| 95 05379 | 2/1995 | WIPO . |

*Primary Examiner*—D. Gabrielle Brouillette
*Attorney, Agent, or Firm*—Arleen Palmberg; David E. Boone

[57] ABSTRACT

The present invention provides a method for treating a condition associated with muscarinic receptor modulation using a 3-[4-(butylthio)-1,2,5-thiadiazol-3-yl]-1-azabicyclo-[2.2.2]octane transdermal formulation. The invention provides desired transdermal 3-[4-(butylthio)-1,2,5-thiadiazol-3-yl]-1-azabicyclo[2.2.2]octane patch formulations.

13 Claims, No Drawings

TRANSDERMAL FORMULATION

This application is a continuation of application Ser. No. 08/481,016, filed on Jun. 7, 1995, now abandoned which in turn is a continuation-in-part of application Ser. No. 08/390,445, filed on Feb. 17, 1995, now abandoned.

FIELD OF THE INVENTION

The present invention provides a novel transdermal formulation containing the pharmaceutically active compound 3-[4-(butylthio)-1,2,5-thiadiazol-3-yl]-1-azabicyclo[2.2.2]octane.

BACKGROUND OF THE INVENTION

The compound 3-[4-(butylthio)-1,2,5-thiadiazol-3-yl]-1-azabicyclo[2.2.2]octane, described in U.S. Pat. No. 5,260,314 ('314), is a compound having muscarinic activity which is indicated for the treatment of Alzheimer's Disease, severe painful conditions, schizophrenia and glaucoma. As set forth in the '314 patent, 3-[4-(butylthio)-1,2,5-thiadiazol-3-yl]-1-azabicyclo[2.2.2]octane can be prepared in a solid form for oral use, in the form of suppositories for rectal administration, or in the form of sterile injectable solutions for parenteral use. A formulation for a typical tablet is provided; however, the patent does not suggest that it would be possible or desirable to prepare a transdermal 3-[4-(butylthio)-1,2,5-thiadiazol-3-yl]-1-azabicyclo[2.2.2]octane patch formulation.

Applicants have discovered that the transdermal 3-[4-(butylthio)-1,2,5-thiadiazol-3-yl]-1-azabicyclo[2.2.2]octane patch formulation of this invention provides surprising beneficial effects. The present invention provides a method for treating Alzheimer's disease and severe painful conditions with fewer side effects than are typically associated with muscarinic agonists like 3-[4-(butylthio)-1,2,5-thiadiazol-3-yl]-1-azabicyclo[2.2.2]octane. The transdermal formulation of this invention provides consistent dosage of the active ingredient, achieves sustained plasma concentration of the pharmaceutically active agent, and encourages patient compliance.

SUMMARY OF THE INVENTION

The present invention provides a transdermal 3-[4-(butylthio)-1,2,5-thiadiazol-3-yl]-1-azabicyclo[2.2.2]octane patch formulation comprising an effective amount of 3-[4-(butylthio)-1,2,5-thiadiazol-3-yl]-1-azabicyclo[2.2.2]octane, from 0.1 to 10 parts by weight azone, from 30 to 69.8 parts by weight ethanol, 29 to 50 parts by weight water, from 0 to 30 parts by weight propylene glycol, and 1 to 5 parts by weight Klucel HF™.

Further, there is provided a transdermal 3-[4-(butylthio)-1,2,5-thiadiazol-3-yl]-1-azabicyclo[2.2.2]octane patch formulation comprising an effective amount of 3-[4-(butylthio)-1,2,5-thiadiazol-3-yl]-1-azabicyclo[2.2.2]octane and from about 70 to 99.8% by weight acrylate adhesive. There is provided a transdermal patch wherein 3-[4-(butylthio)-1,2,5-thiadiazol-3-yl]-1-azabicyclo[2.2.2]octane is intimately distributed in a matrix.

Additionally, there is provided a transdermal 3-[4-(butylthio)-1,2,5-thiadiazol-3-yl]-1-azabicyclo[2.2.2]octane patch formulation comprising an effective amount of 3-[4-(butylthio)-1,2,5-thiadiazol-3-yl]-1-azabicyclo[2.2.2]octane, from 85 to 97 parts by weight ethanol and from 2 to 14.9 parts by weight Klucel HF™.

Finally, there is provided a method for treating a condition associated with the modulation of a muscarinic receptor comprising administering 3-[4-(butylthio)-1,2,5-thiadiazol-3-yl]-1-azabicyclo[2.2.2]octane transdermally using a patch formulation.

DETAILED DESCRIPTION OF THE INVENTION

As used herein "3-[4-(butylthio)-1,2,5-thiadiazol-3-yl]-1-azabicyclo[2.2.2]octane" shall refer to the free base, a pharmaceutically acceptable salt or solvate there of. The free base is preferred. The free base of the compound has the following structure:

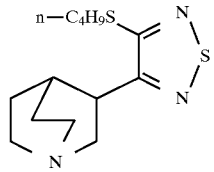

The transdermal 3-[4-(butylthio)-1,2,5-thiadiazol-3-yl]-1-azabicyclo[2.2.2]octane patch formulations of the present invention provide surprising beneficial properties. The 3-[4-(butylthio)-1,2,5-thiadiazol-3-yl]-1-azabicyclo[2.2.2]octane tablet can be associated with undesired parasympathomimetic or -lytic effects when administered to humans. Applicants have discovered that the transdermal patch formulation can minimize such effects while providing higher sustained plasma levels of the pharmaceutically active agent.

Although the transdermal patch formulations claimed herein are preferred for the transdermal delivery of 3-[4-(butylthio)-1,2,5-thiadiazol-3-yl]-1-azabicyclo[2.2.2]octane, other transdermal formulations may be employed. Percutaneous or transdermal delivery of pharmacologically active agents has become feasible in recent years largely due to vehicles therefor which allow increased permeation of said agents into the body surface to which applied. Such agents which may be useful for the preparation of a 3-[4-(butylthio)-1,2,5-thiadiazol-3-yl]-1-azabicyclo[2.2.2]octane transdermal patch formulation include, but are not necessarily limited to, dimethylsulfoxide (U.S. Pat. No. 3,551,554); various 1-substituted azacycloalkan-2-ones such as azone (U.S. Pat. Nos. 4,562,075, 4,405,616, 4,326,893 and 3,989,816); sugar esters in combination with sulfoxide or phosphine oxide (U.S. Pat. Nos. 4,130,667, 4,130,643, 4,046,886, 3,952,099, and 3,896,238); lower alkyl amides (U.S. Pat. No. 3,472,931); certain aliphatic sulfoxides (U.S. Pat. No. 3,903,256); a composition containing glycerol monooleate, ethanol and isopropyl myristate (U.S. Pat. No. 4,335,115); a binary mixture of 1-dodecylazacycloheptan-2-one and a compound selected from a diol or a second N-substituted azacycloalkyl-2-one (U.S. Pat. No. 4,557,934); and polyethylene glycol monolaurate (U.S. Pat. No. 4,568,343). U.S. Pat. Nos. 3,551,554, 4,562,075, 4,405,616, 4,326,893, 3,989,816, 4,130,667, 4,130,643, 4,046,886, 3,952,099, 3,896,238, 3,472,931, 3,903,256, 4,335,115, 4,557,934, and 4,568,343 are hereby incorporated by reference in their entirety.

It is contemplated that the transdermal patch formulations of this invention will find utility in both humans and animals, i.e., will have both medical and veterinary applications for providing increased percutaneous absorption of the pharmaceutically active agent. As used herein, the term "percutaneous" refers to the passage of such agents through skin (typically intact).

The transdermal formulations of the present invention may be administered using a variety of devices which have been described in the art. For example, such devices include, but are not limited to those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, and 4,292,303 each of which is hereby incorporated by reference in its entirety. The dosage forms of the present invention may incorporate certain pharmaceutically acceptable excipients which are conventional in the art. These include, but are not limited to, gelling agents, cream and ointment bases, and the like.

The 3-[4-(butylthio)-1,2,5-thiadiazol-3-yl]-1-azabicyclo [2.2.2]octane shall be present in the claimed dosage forms in an effective amount. The term "an effective amount" shall refer to an amount calculated to achieve and maintain blood levels which will bring about the desired beneficial or therapeutic effect over the period of time desired. These amounts will vary depending upon the amount of pharmacologically active agent required to achieve the desired beneficial or therapeutic effect, whether one or more patches will be administered simultaneously the specific formulation of the patch, the age and condition of the patient to be treated, and the like. Such conventional dosage titration techniques, familiar to the skilled artisan, may be utilized to determine the amount of 3-[4-(butylthio)-1,2,5-thiadiazol-3-yl]-1-azabicyclo[2.2.2]octane present in the ultimate pharmaceutical dosage form for any specific situation. Typically, an effective amount is between about 1 mg to about 100 mg of compound per patch. More preferably, the effective amount is between about 1 mg to about 50 mg of compound. The effective amount may be between about 1 mg and about 300 mg of compound. The amount actually contained in the patch will depend on the factors described as well as the days of treatment provided per patch.

The pharmacologically active 3-[4-(butylthio)-1,2,5-thiadiazol-3-yl]-1-azabicyclo[2.2.2]octane is administered by known techniques such as placing the patch containing said agent and transdermal formulation therefor on a body surface and maintaining said source on said body surface in agent and composition transmitting relation thereto.

One of the transdermal 3-[4-(butylthio)-1,2,5-thiadiazol-3-yl]-1-azabicyclo[2.2.2]octane patch formulations utilizes ethanol, water, azone, and optionally propylene glycol to enhance the permeation of the pharmacologically active 3-[4-(butylthio)-1,2,5-thiadiazol-3-yl]-1-azabicyclo[2.2.2] octane. As noted supra, azone is known to be useful for transdermal permeation enhancement and is chemically 1-dodecylazacyloheptan-2-one. Azone can be prepared as described in U.S. Pat. No. 4,316,893, hereby incorporated by reference.

Formulation of the claimed compositions may be achieved by conventional methods, as by the simple mixing of all components thoroughly. The artisan will appreciate that compositions containing diols other than propylene glycol and alcohols other than ethanol (i.e., 2-propanol) may find utility in transdermal 3-[4-(butylthio)-1,2,5-thiadiazol-3-yl]-1-azabicyclo[2.2.2]octane compositions as a component of the formulation. To the extent that such formulation exhibits the characteristics of the present compositions, such formulations are considered to fall within the scope of the present invention.

The present invention provides a transdermal 3-[4-(butylthio)-1,2,5-thiadiazol-3-yl]-1-azabicyclo[2.2.2]octane patch formulation comprising an effective amount of 3-[4-(butylthio)-1,2,5-thiadiazol-3-yl]-1-azabicyclo[2.2.2] octane, from 0.1 to 10 parts by weight azone, from 30 to 69.8 parts ethanol, 29 to 50 parts by weight water, from 0 to 30 parts by weight propylene glycol, and 1 to 5 parts by weight Klucel HF. Preferred ranges for the formulation include from 2 to 4 parts by weight azone, from 30 to 55 parts by weight ethanol, from 0 to 20 parts by weight propylene glycol, from 35 to 45 parts water, and from 2.5 to 3.5 parts Klucel HF. One preferred embodiment is to omit propylene glycol from the formulation.

There is provided a transdermal formulation patch wherein an effective amount of 3-[4-(butylthio)-1,2,5-thiadiazol-3-yl]-1-azabicyclo[2.2.2]octane is intimately distrubuted in a matrix. One such preferred matrix is a pressure sensitive adhesive.

Further, there is provided a transdermal 3-[4-(butylthio)-1,2,5-thiadiazol-3-yl]-1-azabicyclo[2.2.2]octane patch formulation comprising an effective amount of 3-[4-(butylthio) -1,2,5-thiadiazol-3-yl]-1-azabicyclo[2.2.2]octane and from about 70 to 99.8% acrylate adhesive. A preferred range of acrylic adhesive comprises from about 66 to about 99.8% by weight acrylic adhesive. A further preferred range of acrylic adhesive comprises from about 70 to about 98% by weight acrylic adhesive. Another preferred range for the acrylate adhesive is from about 80 to 98 parts by weight. The acrylate adhesive is commercially available and may be purchased for example, from the National Starch and Chemical Corporation, Bridgewater, N.J. 08807, catalog number 80-1054. The acrylate adhesive typically contains 48% solids in 33% ethyl acetate/28% heptane/34% isopropanol/ 5% toluene by weight. A preferred range for the acrylate adhesive is from about 80 to 98 parts by weight.

Additionally, there is provided a transdermal 3-[4-(butylthio)-1,2,5-thiadiazol-3-yl]-1-azabicyclo[2.2.2]octane patch formulation comprising an effective amount of 3-[4-(butylthio)-1,2,5-thiadiazol-3-yl]-1-azabicyclo[2.2.2] octane, from 85 to 97 parts by weight ethanol and from 2 to 14.9 parts Klucel HF. Klucel HF is a commercially available gelling agent. For example, Klucel HF may be purchased from Aqualon. Other appropriate gelling agents can be selected by the skilled artisan. Preferred ranges for the formulation are 92 to 96 parts by weight ethanol and 2.5 to 3.5 parts Klucel HF or other appropriate gelling agent. Another preferred range for such formulations comprises from about 93 to about 95 parts by weight ethanol and from about 3 to about 3.5 parts gelling agent.

The compound 3-[4-(butylthio)-1,2,5-thiadiazol-3-yl]-1-azabicyclo[2.2.2]octane can be prepared as described in U.S. Pat. No. 5,260,314 Sauerberg et. al. ('314) which is hereby incorporated by reference in its entirety. As disclosed in the '314 patent 3-[4-(butylthio)-1,2,5-thiadiazol-3-yl]-1-azabicyclo[2.2.2]octane can be useful for the treatment of Alzheimer's disease, severe painful conditions, glaucoma, and for the stimulation of cognitive function of the forebrain and hippocampus of mammals.

The 3-[4-(butylthio)-1,2,5-thiadiazol-3-yl]-1-azabicyclo [2.2.2]octane capsule formulation and oral suspension formulation have been administered to patients suffering from a severe painful condition. Such formulations of 3-[4-(butylthio)-1,2,5-thiadiazol-3-yl]-1-azabicyclo[2.2.2]octane can be associated with undesired parasympathomimetic effects when administered to a group of subjects. Surprisingly, the presently claimed transdermal formulations of 3-[4-(butylthio)-1,2,5-thiadiazol-3-yl]-1-azabicyclo [2.2.2]octane minimize or eliminate such effects while maintaining a consistent, desirable plasma concentration of the pharmacologically active agent.

This invention provides a method for treating a condition associated with modulation of a muscarinic receptor with minimal or no parasympathomimetic effects comprising administering 3-[4-(butylthio)-1,2,5-thiadiazol-3-yl]-1-azabicyclo[2.2.2]octane transdermally. Examples of such conditions associated with modulation of a muscarinic receptor include, but are not in any way limited to decreased cognition, Alzheimer's Disease, and severe painful conditions. Preferred transdermal patch formulations include but are not limited to a patch formulation comprising an effective amount of 3-[4-(butylthio)-1,2,5-thiadiazol-3-yl]-1-azabicyclo[2.2.2]octane, azone, ethanol, water, optionally propylene glycol and Klucel HF; an effective amount of 3-[4-(butylthio)-1,2,5-thiadiazol-3-yl]-1-azabicyclo[2.2.2]octane intimately distributed in a matrix; an effective amount of 3-[4-(butylthio)-1,2,5-thiadiazol-3-yl]-1-azabicyclo[2.2.2]octane and an acrylic adhesive; an effective amount of 3-[4-(butylthio)-1,2,5-thiadiazol-3-yl]-1-azabicyclo[2.2.2]octane, ethanol, and Klucel HF; described herein.

As reported herein, plasma levels are determined using gas chromatography methods familiar to the skilled artisan. The artisan can establish the appropriate conditions for the gas chromatographic analysis; however, one set of suggested conditions include the following:

A 30 cm×0.25 $\mu$m capillary column (J & W Scientific for example); hydrogen flow rate of 3.2 ml/min, helium flow rate of 14.3 ml/min, and air flow of 115.0 ml/min. The gradient column temperature is suggested to be 90° to 270° C., detector at 250° C., and injector at 250° C. A suggested detection type is nitrogen-phosphorus. The artisan will recognize that other conditions will be effective as well; however, the present conditions are provided as guidance to assist the artisan in choosing the most desired parameters for the present conditions.

It shall be understood that other suitable enhancers and substances beneficial to the drug substance skin flow may preferably be included in the formulations claimed herein.

The following examples are provided to more fully illustrate the invention claimed herein. The examples are provided for illustrative purposes only and are not intended to limit the scope of the invention in any way.

EXAMPLE 1

Transdermal Formulation Free Base

A 0.5 g sample of 3-[4-(butylthio)-1,2,5-thiadiazol-3-yl]-1-azabicyclo[2.2.2]octane free base is dissolved in 9.25 g of ethanol (200 proof). A 0.75 g sample of azone and a 5.0 g aliquot of propylene glycol are added to the ethanol mixture with stirring. A 10 g sample of water is added to the mixture. Finally, 0.75 g of Klucel is added to the mixture and stirred until the Klucel is dispersed. The mixture is allowed to stand for 24 hours. A 2.0 g sample of the formulation prepared as described herein is dispensed by syringe into a reservoir-type transdermal adhesive system. The patch formulation, prepared as described, is applied to the shaved skin of a dog. The concentration of drug substance as measured by ng/ml of Dog plasma is monitored at 0, 3,6,9, 12, 15, 24, 32, and 48 hours after application of the patch. The concentration of drug substance in the dog plasma demonstrates that the transdermal formulation effectively delivers the drug across the skin barrier.

EXAMPLE 2

Transdermal Formulation without Polyethylene Glycol

A 0.5 g sample of 3-[4-(butylthio)-1,2,5-thiadiazol-3-yl]-1-azabicyclo[2.2.2]octane free base is dissolved in 13.0 g of ethanol (200 proof). A 0.75 g sample of azone is added to the ethanol mixture with stirring. An 11.25 g sample of water is added to the mixture. Finally, 0.75 g of Klucel is added to the mixture and stirred until the Klucel is dispersed. The mixture is allowed to stand for 24 hours. A 2.0 g sample of the formulation prepared as described herein is dispensed by syringe into a reservoir-type transdermal adhesive system. The patch formulation, prepared as described, is applied to the shaved skin of a dog. The passage of drug substance across the skin barrier can be demonstrated by monitoring the concentration of drug substance in dog plasma (ng/ml) at 0,3,6,9,12,15,24,28,32, and 48 hours after application of the patch. The passage of the drug substance across the skin can be confirmed by applying a patch prepared as described herein to the shaved chest of a monkey. The patch may be removed and additional plasma samples taken to demonstrate that the amount of drug substance will decrease with time.

EXAMPLE 3

Transdermal 3-[4-(butylthio)-1,2,5-thiadiazol-3-yl]-1-azabicyclo[2.2.2]octane in Acrylic Adhesive A 600 mg sample of 3-[4-(butylthio)-1,2,5-thiadiazol-3-yl]-1-azabicyclo[2.2.2]octane free base is dissolved in 41.6 g of pressure sensitive acrylic adhesive (cat. number 80-1054, National Starch and Chemical Corporation, Bridgewater, N.J. 08807). The mixture is agitated for 2 hours on a three roller mill. The mixture is coated along the length of a 3 mil thick release liner using a knife coater providing a 20 mil gap. The 20 mil gap provides an effective 20 mil thick coating of the formulation on the release liner. The sample is allowed to air dry for 24 hours. The sample is laminated on polyester backing.

The patches prepared as stated herein are applied to rats. The rats are killed in pairs at various time points after application and the rat brains are removed and frozen. The binding of the M1 antagonist ligand, $^3$H-pirenzepine, to muscarinic receptors in the brain is determined. The decrease in binding is indicative of drug or active metabolite present in the brain. The effect of the drug after oral administration lasts less than 6 hours. The percent of control ex vivo pirenzepine binding is monitored at 6 hours, 12 hours, 24 hours, and 48 hours.

Further, patches prepared as described herein are applied to the shaved skin of a dog and dog plasma levels (ng/ml) are monitored at 0,3,6,9,12,15,24,28,32, and 48 hours after application of the patch. The passage of the drug substance across the skin can be confirmed by applying a patch prepared as described herein to the shaved chest of a monkey. The patch may be removed and additional plasma samples taken to demonstrate that the amount of drug substance will decrease with time.

EXAMPLE 4

Transdermal 3-[4-(butylthio)-1,2,5-thiadiazol-3-yl]-1-azabicyclo[2.2.2]octane in Gel A 1.0 g sample of 3-[4-(butylthio)-1,2,5-thiadiazol-3-yl]-1-azabicyclo[2.2.2]octane free base is dissolved in 47.5 g of ethanol (200-proof). Then a 1.5 g sample of Klucel gelling agent is added to the solution and stirred until dispersed. The gel is allowed to stand for 24 hours. A 2.0 g sample of the formulation prepared as such is dispensed by syringe into a reservoir-type transdermal adhesive system.

The patches prepared as stated herein are applied to rats. The rats are killed in pairs at various time points after application and the rat brains are removed and frozen. The binding of the M1 antagonist ligand, $^3$H-pirenzepine, to muscarinic receptors in the brain is determined. The decrease in binding is indicative of drug or active metabolite present in the brain. The effect of the drug after oral administration lasts less than 6 hours. The percent of control ex vivo pirenzepine binding is monitored at 6 hours, 12 hours, 24 hours, and 48 hours.

Further, patches prepared as described herein are applied to the shaved skin of a dog and dog plasma levels (ng/ml) are monitored at 0,3,6,9,12,15,24,28,32, and 48 hours after application of the patch. The passage of the drug substance across the skin can be confirmed by applying a patch prepared as described herein to the shaved chest of a monkey. The patch may be removed and additional plasma samples taken to demonstrate that the amount of drug substance will decrease with time.

EXAMPLE 5

Transdermal 3-[4-(butylthio)-1,2,5-thiadiazol-3-yl]-1-azabicyclo[2.2.2]octane

Studies were conducted to evaluate the transdermal delivery of 3-[4-(butylthio)-1,2,5-thiadiazol-3-yl]-1-azabicyclo[2.2.2]octane in rat skin. Rats were administered either 5 mg/kg of 3-[4-(butylthio)-1,2,5-thiadiazol-3-yl]-1-azabicyclo[2.2.2]octane by the transdermal route or the subcutaneous route. Plasma samples were collected at various time intervals (0.5–28 hr) and assayed for parent drug content. With the subcutaneous administration of 3-[4-(butylthio)-1,2,5-thiadiazol-3-yl]-1-azabicyclo[2.2.2]octane, a peak plasma concentration of 83.9 ng/ml was reached at 0.5 hr and plasma concentrations declined thereafter. In contrast, transdermal administration of 3-[4-(butylthio)-1,2,5-thiadiazol-3-yl]-1-azabicyclo[2.2.2]octane yielded a plasma concentration maximum of 18.2 ng/ml at 4 hr and plasma concentrations were sustained over several hours. Comparison of the plasma concentration (area under the curve measurement) of parent compound by these different administration routes suggests that at least 68% of the dose administered by the transdermal route is absorbed. These data demonstrate that 3-[4-(butylthio)-1,2,5-thiadiazol-3-yl]-1-azabicyclo[2.2.2]octane readily penetrated the skin and was absorbed into the blood.

Plasma Concentrations of 3-[4-(butylthio)-1,2,5-thiadiazol-3-yl]-1-azabicyclo[2.2.2]octane following transdermal or subcutaneous administration.

| Time (hr) | Transdermal ng/ml of Plasma | trans-sem* (Standard error of the mean) | SC ng/ml of Plasma | sc-sem (Standard error of the mean) |
|---|---|---|---|---|
| 0.5 | 4.34 | 5 | 83.87 | 39.09 |
| 1 | 5.11 | 4.55 | 60.01 | 21.13 |
| 2 | 12.36 | 4.35 | 58.75 | 7.05 |
| 4 | 18.17 | 5.36 | 18.99 | 6.88 |
| 6 | 13.52 | 5.87 | 13.49 | 2.05 |
| 8 | 15.67 | 5.61 | 8.34 | 2.08 |
| 12 | 6.69 | 1.95 | 2.67 | 0.35 |
| 24 | 2.4 | 2.08 | 0.89 | 0.78 |
| 28 | 2.54 | | | |

We claim:

1. A transdermal patch prepared using a formulation comprising from about 66 to 99.8% acrylate adhesive, and the compound 3-[4-(butylthio)-1,2,5-thiadiazol-3-yl]-1-azabicyclo[2.2.2]octane in an amount so that the patch contains between about 1 to about 100 mg of the compound.

2. A transdermal patch prepared using a formulation comprising the compound 3-[4-(butylthio)-1,2,5-thiadiazol-3-yl]-1-azabicyclo[2.2.2]octane in an amount so that the patch contains between about 1 to about 100 mg of the compound distributed in a matrix comprising a pressure-sensitive adhesive.

3. A method for treating a condition associated with modulation of a muscarinic receptor comprising administering 3-[4-(butylthio)-1,2,5-thiadiazol-3-yl]-1-azabicyclo[2.2.2]octane using a transdermal patch.

4. A method for treating a condition associated with modulation of a muscarinic receptor comprising administering 3-[4-(butylthio)-1,2,5-thiadiazol-3-yl]-1-azabicyclo[2.2.2]octane transdermally using a patch formulation of claim 1.

5. A method of claim 4 wherein the condition is decreased cognition.

6. A method of claim 4 wherein the condition is Alzheimer's disease.

7. A method of claim 4 wherein an analgesic effect is desired for the treatment of a severely painful condition.

8. A method for treating a condition associated with modulation of a muscarinic receptor comprising administering 3-[4-(butylthio)-1,2,5-thiadiazol-3-yl]-1-azabicyclo[2.2.2]octane transdermally using a patch formulation of claim 2.

9. A transdermal patch of claim 2 wherein the pressure-sensitive adhesive is an acrylic adhesive.

10. A transdermal patch of claim 2 which contains a permeation enhancer.

11. A transdermal patch of claim 2 wherein the amount of compound is from 0.1 to 35% by weight of the matrix.

12. A transdermal patch of claim 1 wherein the formulation contains from about 80–98% acrylic adhesive.

13. A transdermal patch of claim 12 wherein the formulation provides about 1 to about 50 mg of compound per patch.

* * * * *